US00PP33701P2

(12) United States Plant Patent
Clark

(10) Patent No.: US PP33,701 P2
(45) Date of Patent: Nov. 30, 2021

(54) BLACKBERRY PLANT NAMED 'A-2524T'

(50) Latin Name: *Rubus subgenus Rubus Watson*
Varietal Denomination: A-2524T

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/120,550

(22) Filed: Dec. 14, 2020

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
See application file for complete search history.

*Primary Examiner* — Annette H Para
(74) *Attorney, Agent, or Firm* — Quarles & Brady LLP

(57) ABSTRACT

Description and specifications of a new and distinct cultivar of blackberry plant originated from a hand-pollinated cross of 'Ark. 2271T' (a non-patented, unreleased genotype) x 'Ark. 2252T' (a non-patented, unreleased genotype). This new cultivar of blackberry plant can be distinguished by its long-shaped, large berries, good flavor, high productivity, and very healthy plants.

3 Drawing Sheets

Latin name: *Rubus* subgenus *Rubus* Watson.
Varietal denomination: 'A-2524T'.

BACKGROUND

The new floricane-fruiting cultivar of blackberry called 'A-2524T' is described herein. The new cultivar originated from a hand-pollinated cross of 'Ark. 2271T' (a non-patented, unreleased genotype) x 'Ark. 2252T' (a non-patented, unreleased genotype) made in 2009. The seeds resulting from this controlled hybridization were germinated in a greenhouse in the spring of 2010 and planted in a field near Clarksville, Ark. (West-Central Arkansas). The seedlings fruited in the summer of 2012 and one seedling, designated 'Ark. 2524T', was selected for its long-shaped, large berries, good flavor, high productivity, and very healthy plants.

SUMMARY OF THE INVENTION

This new and distinct cultivar of blackberry originated from a hand-pollinated cross of 'Ark. 2271T' (a non-patented, unreleased genotype) x 'Ark. 2252T' (a non-patented, unreleased genotype) made in 2009 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2010 and planted in a field near Clarksville, Ark. The seedlings fruited in the summer of 2012 on floricanes and one seedling, designated 'Ark. 2524T,' was selected for long-shaped, large berries, good flavor, high productivity, and very healthy plants.

During 2012, the original plant selection was propagated asexually from root cuttings at the above-noted location, and a test row of 20 plants was established. Subsequently, larger test plantings have been established with asexually multiplied plants at one location in Arkansas.

The new cultivar has been asexually multiplied annually since 2012 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants from which the images were taken were 3 years old.

DETAILED DESCRIPTION OF THE NEW CULTIVAR 'A-2524T'

Figure 1:
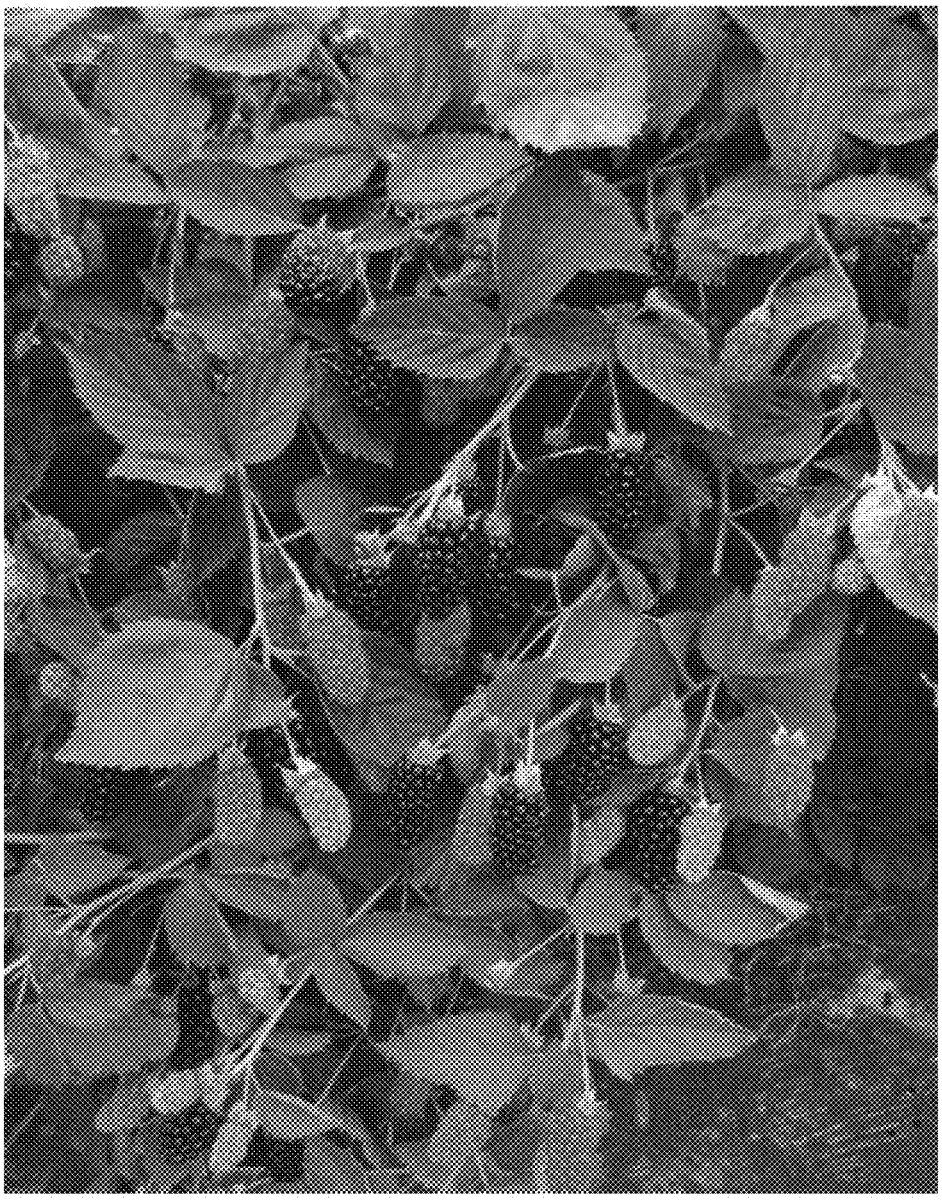
FIG. 1 is a photograph of blackberry canes of 'A-2524T' with ripe fruit on the plant.
Figure 2:
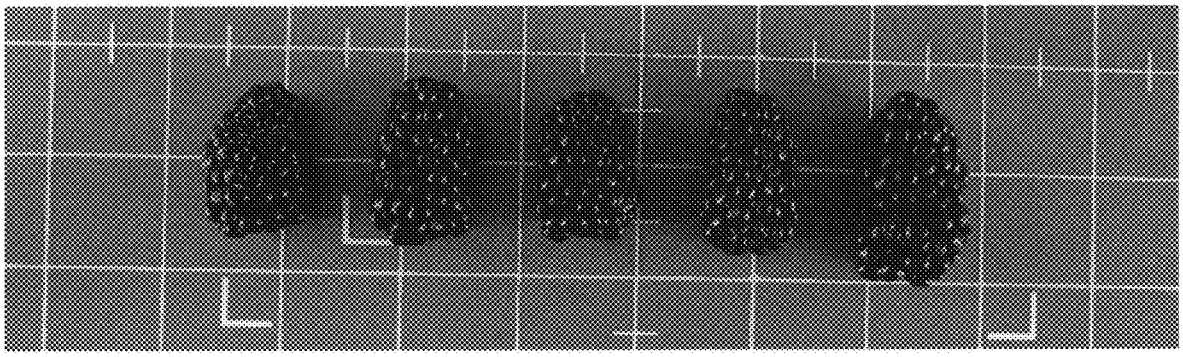
FIG. 2 is a photograph of ripe fruit of 'A-2524T'.
Figure 3:
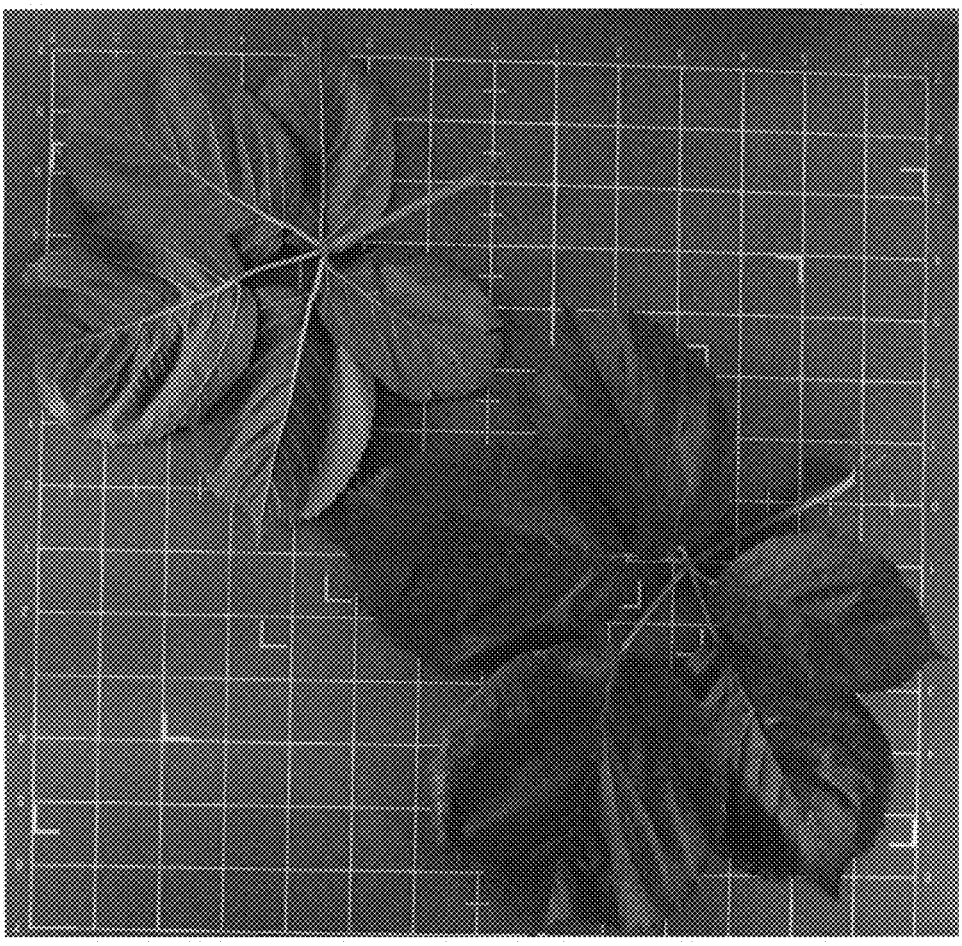
FIG. 3 is a photograph showing the abaxial and adaxial sides of a primocane leaf of 'A-2524T'.

Plants and fruit of this new cultivar differ phenotypically from its parents. The new cultivar is larger in fruit size, has better flavor and is more productive than its female parent 'Ark. 2271T.' The new cultivar is earlier ripening, larger, has better flavor and is more productive than its male parent 'Ark. 2252T.' Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are very erect in growth habit. The canes can be trained to a self-supporting hedgerow although it is beneficial to use a trellis with supporting wires to prevent canes from collapsing due to wind or heavy fruit loads. The plants are thornless. Plants and fruit have shown no susceptibility to anthracnose [*Elsinoe veneta* (Burkh.) Jenkins], and plants have shown no evidence of susceptibility to orange rust [*Gymnoconia nitens* (Schwein.) F. Kern and H. W. Thurston.]. Plants have shown no susceptibility to cane and leaf rust (*Kuehneola uredines* (Link) Arthur). No screening has been done for resistance to double blossom/rosette [*Cercosporella rubi* (Wint.) Plakidas].

The bloom period of the new cultivar begins on average 16 April for 10% bloom and 25 April for 50% bloom and was very near that of 'Osage' (U.S. Plant Pat. No. 26,120) and later than 'Natchez' (U.S. Plant Pat. No. 20,891).

Fruit of the new cultivar has an average first harvest date of 7 June and was three days after 'Osage' and five days later than 'Natchez'. The floricane fruiting period is long, averaging 61 days. Fruit yields of the new cultivar on floricanes are very high and on average 8.6 kg (18.9 lb/plant), higher than that for 'Osage' and 'Natchez', in West-Central Arkansas. 'A-2524T' does not produce fruit on primocanes.

The fruit is elongated in shape and glossy with a uniform black finish. The floricane fruit is large (ave. 7.9 g), 3 g larger than 'Osage', and 1.0 g smaller than 'Natchez'. Fruit size of the new cultivar is maintained well throughout the entire harvest season. The new cultivar exhibits excellent fruit fertility with full drupelet set. Storage potential of fresh fruit of the new cultivar is lower than that of 'Osage' and 'Natchez' due to softer fruit with more leakage in storage than these cultivars.

The dry seed weight for the new cultivar averaged 4.5 mg/seed, slightly larger than 'Osage' and smaller than 'Natchez'.

The fresh fruit rates very well in flavor and when fully ripe are very sweet with good aromatic components. The soluble solids concentration averages 8.7% on shiny black fruit, which is lower than 'Osage', and 'Natchez'. Titratable acidity averages 1.10 g/L (expressed as citric acid) and is higher than that for 'Osage' (0.89 g/L) and comparable to 'Natchez' (1.14 g/L). Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Color Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with drip irrigation at or near Clarksville, Ark. The plants were fertilized near budbreak (late March on average) with complete or nitrogen fertilizer and had an additional nitrogen fertilizer application in early July. Primocanes were tipped at approximately 1.14 m (45 inches) and grown in a hedgerow training system including a trellis. Weeds were controlled with pre- and post-emergent herbicides supplemented with mechanical weed control activities. A single application of liquid lime sulfur was applied to the plants at budbreak, and two additional fungicide applications applied near bloom and one to two weeks later. Insecticides were used for spotted-wing drosophila (*Drosophila suzukii* Matsumura) control during the harvest season. The descriptions reported herein are from specimens grown near Clarksville, Ark.

Plant:

*Size.*—Medium to large. Plants are grown in a hedgerow and primocanes tipped at approximately 1.14 m; plants in this system range in size from approx. 107-140 cm tall and 91-102 cm wide.

*Growth habit.*—Upright, moderate to high vigor, canes erect; suckers from the crown and roots.

*Growth rate.*—Floricane first budbreak 18 February. First emergence of primocanes is 28 April and primocanes reach tipping height (107 cm) on 7 May.

Productivity:

*Floricane.*—8.6 kg (18.9 lb/plant). The low temperature of 1° F. was the lowest the cultivar has been exposed to and fruited successfully after this exposure. Cold hardiness: Hardy to 1.0° F. (−17° C.).

Canes: Thornless, erect.

*Floricane* (*dormant or winter cane*).—Cane: diameter: Base 0.78 cm; midpoint 0.67 cm; terminal 0.64 cm. Internode length: Base 3.93 cm; midpoint 5.35 cm; terminal 4.60 cm. Floricane color: Base yellow-green group 145B; midpoint yellow-green group 145B; terminus yellow-green group 145B. Thorn density (per 30 cm of cane length): None, this plant is thornless. Glandular hairs on young shoots: Absent or few. Dormant cane shape (cross section): Angular.

*Primocane* (*current-season cane; late summer*).—Cane: Diameter: base 1.27 cm; midpoint 1.29 cm; terminal 0.55 cm. Internode length: Base 9.48 cm; midpoint 12.21 cm; terminal 4.11 cm. Primocane color: Base green group 143B; midpoint yellow-green group 144A: terminus yellow-green group 144B. Anthocyanin coloration present on floricanes and primocanes with color most prevalent on sun-exposed canes towards the top of the canopy. Thorn density (per 30 cm of cane length): None, this plant is thornless. Glandular hairs on young shoots: Absent or few. Disease resistance: Plants and fruit have shown no susceptibility to anthracnose, and plants have shown no evidence of susceptibility to orange rust. Plants have shown no susceptibility to cane and leaf rust. No screening has been done for resistance to double blossom/rosette. Lateral branching after tipping (measured at the end of growing season): Average number of lateral branches: 4; distribution concentrated on the distal portion (top one-third) of the canes.

Foliage:

*Primocane.*—Average date of leaf bud burst: Primocane buds open as the cane emerges, primocane emergence averages 28 April. Average number of primocane produced each growing season: 5. Leaves: Large; mature compound leaf width 24.24 cm; length 21.21 cm; overall shape: palmate. Glossiness: Abaxial: dull, not glossy; adaxial: dull, not glossy. Color: Base abaxial green group 138A; adaxial green group 137A; midpoint abaxial green group 138A; adaxial green group 137A; terminal abaxial green group 138A; adaxial green group 137A. Terminal leaflet: Width 10.19 cm; length 10.97 cm; shape ovate with acute apex and rounded at the base; margin is serrated; serration teeth length is 0.18 cm and width is 0.23 cm; number of leaflets per compound leaf 5; venation pinnate; young leaf abaxial vein color yellow-green group 146C; young leaf adaxial vein color yellow-green group 146B; mature leaf abaxial leaf vein color yellow-green group 145A; mature leaf adaxial vein color yellow-green group 145B; lobing: absent; shape in cross section: u-shaped; degree of blistering between veins: absent to weak; degree of undulation at margin: absent. Petioles: Length: 6.36 cm; color: abaxial yellow-green group 145A; adaxial yellow-green group 145A; diameter 0.36 cm; texture is mostly smooth, exhibiting light pubescence. Petiolules: Length: 3.73 cm; diameter 0.20 cm; color: abaxial yellow-green group 145B and adaxial yellow-green group 145B; texture is light pubescence. Stipules: 2 per leaf; length: 1.39 cm; width: 0.10 cm; texture: pubescence is light on the abaxial surface and absent on the adaxial surface; shape: overall shape is subulate; apex acuminate; base rounded; margins are smooth; color: abaxial yellow-green group 145B, adaxial color green group 143A.

*Floricane.*—Leaves: Large; mature compound leaf width 10.24 cm; length 9.75 cm; overall shape: trifoliate. Average date of leaf bud burst: 18 February. Glossiness: Abaxial: dull, not glossy; adaxial: dull, not glossy. Color: Base abaxial green group 138A; adaxial green group 137A; midpoint abaxial green group 138A; adaxial green group 137A: terminal abaxial green group 138A; adaxial green group 137A. Terminal leaflet: Width 4.57 cm; length 6.23 cm; shape ovate with acute apex and oblique at the base; margin is bi-serrate; serration teeth length is 0.42 cm and width is 0.41 cm; number of leaflets per compound leaf 3; venation pinnate; young leaf abaxial vein color yellow-green group 149A; young leaf adaxial vein color yellow-green group 149C; mature leaf abaxial leaf vein color yellow-green group 145B; mature leaf adaxial vein color yellow-green group 149B; lobing: absent; shape in cross section: u-shaped; degree of blistering between veins: absent to weak; degree of undulation at margin: absent. Petioles: Length 2.50 cm; color: abaxial side is yellow-green group 145B; adaxial surface is yellow-green group 145B; diameter 0.18 cm; texture smooth, light pubescence present. Petiolules: Length 0.90 cm; diameter 0.18 cm; color: abaxial surface is yellow-green group 145B; adaxial surface is yellow-green group 145B; texture: smooth with light pubescence. Stipules: 2 per leaf; length 0.80 cm; width: 0.18 cm; texture: pubescence is light on the abaxial surface and absent on the adaxial surface; shape: overall subulate; apex acuminate; base rounded; margins are smooth; color: abaxial surface green group 137C, adaxial surface green group 137B.

Flowers:

*Floricane.*—Date of bloom: First bloom: 16 April; 50% bloom 25 April. Reproductive organs: Stamens — erect, numerous. Pistils — numerous. Pollen — normal, fertile, and abundant.

*Flower.*—Diameter: 4.41 cm; depth: 1.88 cm; shape: overall rotate; symmetry: actinomorphic.

*Petals.*—Number per flower: 6; length 2.30 cm; width 1.61 cm; shape: apex: obtuse; margin: entire (smooth); base: rounded; color: abaxial surface white group 155D; adaxial surface white group 155D; texture: abaxial: smooth, no pubescence; adaxial: smooth, no pubescence.

*Flowers per cluster.*—6.

*Sepal.*—Number per flower: 5; length 1.22 cm; width: 0.52 cm; shape: overall: deltoid; apex: acuminate; margin: entire (smooth); base: truncate; texture: abaxial: moderate pubescence; adaxial: heavy pubescence; color: abaxial: yellow-green group 146B with greyed-orange group 177A on the tips; adaxial: yellow-green group 146D.

*Pedicel.*—Length: 4.47 cm; width: 0.12 cm; color: yellow-green group 146B; texture: moderate to heavy pubescence.

*Peduncle.*—Length: 0.32 cm; width: 0.45 cm; color: greyed-orange group 166A.

*Cyme.*—Type: elongated simple cyme; length: 10.08 cm.

Fruit:

*Maturity.*—Average first ripe date 7 June; Average fruiting period 61 days.

*Size.*—Large, average 7.9 g.

*Diameter of fruit at primary position on inflorescence.*—Equator 1.95 cm; base pole 1.93 cm; terminal pole 1.50 cm.

*Diameter of fruit at secondary positions on inflorescence.*—Equator 2.03 cm; base pole 1.94 cm; terminal pole 1.61 cm.

*Primary fruit.*—Length: 3.50 cm; shape: narrow ovate to oblong; color: black group 202A.

*Drupelet size.*—0.49 cm.

*Drupelet number per fruit.*—93.

*Seed.*—Average length 0.36 cm; width 0.21 cm; dry weight 4.50 mg; wet weight 5.30 mg; color wet orange-red group 34B; color dry greyed-orange group 165D.

*Soluble solids.*—8.7%.

*pH.*—3.34.

*Titratable acidity.*—1.10 g/L expressed as citric acid.

*Processed quality.—Not evaluated for processing.*

*Uses.*—Home garden cultivar use due to high productivity, long period of fruiting and very healthy plants. Not for commercial shipping use.

The cultivar: The most distinctive features of the cultivar are long-shaped, large berries, good flavor, high productivity, and very healthy plants.

I claim:

1. A new and distinct cultivar of blackberry plant named 'A-2524T' substantially as illustrated and described herein.

* * * * *